United States Patent [19]
Nagai

[11] Patent Number: 5,087,699
[45] Date of Patent: Feb. 11, 1992

[54] 3,4-PYRIDINE-DITHIOL COMPOUNDS AND METHOD OF PRODUCING THE SAME
[75] Inventor: Kazukiyo Nagai, Numazu, Japan
[73] Assignee: Ricoh Company, Ltd., Tokyo, Japan
[21] Appl. No.: 551,204
[22] Filed: Jul. 11, 1990
[30] Foreign Application Priority Data
  Jul. 18, 1989 [JP] Japan .................. 1-185678
[51] Int. Cl.$^5$ .................. C07D 213/26; C07D 213/70
[52] U.S. Cl. .................. 546/296; 546/345; 546/346
[58] Field of Search .................. 546/296
[56] References Cited
U.S. PATENT DOCUMENTS
  4,661,114 4/1987 Konrad et al. .................. 8/409

Primary Examiner—Alan L. Rotman
Attorney, Agent, or Firm—Cooper & Dunham

[57] ABSTRACT

A 3,4-pyridine-dithiol compound having formula (I):

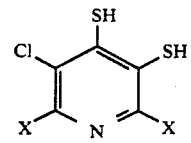

(I)

wherein X is chlorine or a trifluoromethyl group; and a method of producing the above 3,4-pyridine-dithiol compound having formula (I) by allowing a polyhalogenide pyridine compound having formula (II) to react with a hydrosulfide in a polar organic solvent in the presence of sulfur, and an iron powder or an iron salt:

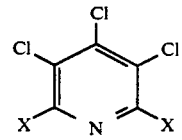

(II)

wherein X is chlorine or a trifluoromethyl group.

5 Claims, 7 Drawing Sheets

3,4-PYRIDINE-DITHIOL COMPOUNDS AND METHOD OF PRODUCING THE SAME

BACKGROUND OF THE INVENTION

1. Field of the Invention

This invention relates to novel 3,4-pyridine-dithiol compounds, and in particular to pyridinethiol compounds which are useful as intermediates for producing pyridinethiolate nickel complexes used as light stabilizers and near-infrared-rays absorbing materials, and useful as chelating agents to obtain dithiolate metal complexes, and a method of producing the 3,4-pyridine-dithiol compounds.

2. Discussion of Background

As the recent development of infrared filters, optical recording media, liquid crystal display devices, laser printers and electrophotographic copying apparatus, the development of a dye which is capable of efficiently absorbing the light in the region of infrared to near infrared is desired.

As the above-mentioned dye which is capable of absorbing the near infrared rays, squarylium dyes, cyanine dyes, metal phthalocyanine dyes and platinum bis(dithio-α-diketone) complex compounds are conventionally known.

The squarylium dyes have the shortcomings that the absorbance thereof is low and the film-forming properties thereof are unsatisfactory.

The cyanine dyes become chemically unstable when their molecular chain is lengthened to increase the absorbance in the near infrared region.

The metal phthalocyanine dyes cannot be worked into a thin-film by the solution coating method because of their low solubility in organic solvents. This will considerably restrict the application thereof. In addition, an amorphous film of the metal phthalocyanine dye is readily crystallized.

Platinum bis(dithio-α-diketone) complex compounds have poor film-forming properties and are chemically unstable.

Various benzenethiolate metal complexes are disclosed in Japanese Laid-Open Patent Applications 63-288786, 63-209890 and 63-288785, which serve as light stabilizers in an organic-dye-type optical disk.

However, the above-mentioned benzenethiolate metal complexes cannot be easily coated on a substrate made of a resin with poor resistance to non-aqueous solvents, such as polycarbonate. This is because the benzenethiolate metal complexes are soluble in the non-aqueous solvents, but are not soluble in aqueous solvents such as alcohol-based solvents.

Furthermore, when an optical disk is prepared by using the benzenethiolate metal complexes, the bit error ratio is increased during the repeated operations, which will be accompanied by the decrease in reliability.

As previously described, most of the conventional materials serving as light stabilizers and near-infrared-rays absorbing materials do not satisfy all the requirements at the same time, such as high solubility in organic solvents, high compatibility with resins, good film-forming properties and chemical stability.

It is recently confirmed that pyridinethiolate nickel complexes effectively function as the light stabilizer and near-infrared-rays absorbing material, with all the aforementioned requirements being satisfied.

SUMMARY OF THE INVENTION

Accordingly, an object of the present invention is to provide compounds which are useful as intermediates for producing pyridinethiolate nickel complexes used as light stabilizers and near-infrared-rays absorbing materials, and useful as chelating agents to obtain dithiolate metal complexes.

Another object of the present invention is to provide a preparation method of the above-mentioned compounds.

The first object of the present invention can be achieved by 3,4-pyridine-dithiol compounds having the following formula (I):

wherein X is chlorine or a trifluoromethyl group.

The second object of the present invention can be achieved by allowing a polyhalogenide pyridine compound having the following formula (II) to react with a hydrosulfide in a polar organic solvent in the presence of sulfur, and an iron powder or an iron salt.

wherein X is chlorine or a trifluoromethyl group.

DESCRIPTION OF THE PREFERRED EMBODIMENTS

Hitherto, 2,3-pyridine-dithiol and 3,4-pyridine-dithiol are known as pyridine-dithiol compounds.

The 3,4-pyridine-dithiol compounds according to the present invention represented by formula (I), wherein X is chlorine or a trifluoromethyl group, that is, polyhalogenide-substituted 3,4-pyridine-dithiol compounds are novel materials.

Specific examples of the 3,4-pyridine-dithiol compounds of formula (I) according to the present invention are as follows:

(1) 2,5,6-trichloro-3,4-pyridine-dithiol
(2) 6-trifluoromethyl-2,5-dichloro-3,4-pyridine-dithiol
(3) 2-trifluoromethyl-5,6-dichloro-3,4-pyridine-dithiol The 3,4-pyridine-dithiol compounds of formula (I) can be prepared by allowing a polyhalogenide pyridine compound having the following formula (II) to react with a hydrosulfide in a polar organic solvent in the presence of sulfur, and an iron powder or an iron salt.

wherein X is chlorine or a trifluoromethyl group.

Specific examples of the polyhalogenide pyridine compound of formula (II) include pentachloropyridine and 6-trifluoromethyl-2,3,4,5-tetrachloropyridine.

As the hydrosulfide, sodium hydrosulfide and potassium hydrosulfide are preferably used.

Preferable examples of the iron salt used in the reaction include iron chloride, iron bromide, iron nitrate and iron phosphate.

Examples of the polar organic solvent for use in the present invention include alcohol-based solvents such as n-butanol; amide-based solvents such as dimethylformamide and hexamethylene phosphoamide; and sulfur-based solvents such as dimethyl sulfoxide. Among them, dimethylformamide is the most preferable from the viewpoints of the solubility of the hydrosulfide therein, the solubility of the reaction product therein and the reaction temperature of 120° C. or more.

In the above reaction, it is preferable that 1 mole of the polyhalogenide pyridine compound of formula (II) be allowed to react with 2 moles or more of the hydrosulfide in the presence of 0.2 moles or more of sulfur and 0.5 moles or more of the iron powder or the iron salt.

It is preferable that the reaction temperature be maintained at room temperature to 100° C. during the first 0.5 to 5 hours, and finally be elevated to 100° to 150° C. for 5 hours or more. This is because the above reaction tends to be explosive and the contents may bump if the reaction mixture is heated beyond 100° C. in a short time. The reaction temperature may be increased stepwise or continuously.

The reaction product is obtained in the form of a complex of iron. This iron complex is isolated from the reaction mixture, and then heated in the presence of zinc oxide and a base to decompose the iron complex, followed by acidifying-out, whereby the 3,4-pyridine-dithiol compound according to the present can be obtained.

The thus obtained 3,4-pyridine-dithiol compound according to the present invention has such a strong chelating capability that a pyridinethiolate metal complex can be prepared by allowing the above 3,4-pyridine-dithiol compound to react with a salt of a transition metal such as nickel, palladium or platinum in an appropriate solvent.

Alternatively, in the preparation of the pyridinethiolate metal complex, the 3,4-pyridine-dithiol compound according to the present invention may be converted into an alkali metal salt prior to the reaction with the salt of the transition metal. In this process, the 3,4-pyridine-dithiol compound according to the present invention is changed into the pyridinethiolate metal complex via an alkali metal salt having the following formula (III):

wherein Ms are hydrogen, lithium, sodium or potassium, and when one of Ms represents hydrogen, the other M is an atom other than hydrogen; and X is chlorine or a trifluoromethyl group.

The 3,4-pyridine-dithiol compounds according to the present invention can be converted into alkali metal salts by the conventional methods. For instance, the 3,4-pyridine-dithiol compounds are treated by a strong base, such as sodium hydroxide or potassium hydroxide; or treated by a metal alcoholate which is prepared by conversion of, for example, metallic lithium or metallic sodium in an alcohol solvent.

The pyridinethiolate metal complexes thus obtained from the 3,4-pyridine-dithiol compounds according to the present invention mostly have a univalent or bivalent negative electric charge. Then, the pyridinethiolate metal complexes can be formed into chemically stable metal complexes in combination with appropriate cations. As the cations, quaternary ammonium salts and quaternary phosphonium salts are preferably employed.

As previously explained, the 3,4-pyridine-dithiol compounds of formula (I) according to the present invention, which make it possible to prepare various metal complexes, are useful as intermediates for producing such metal complexes. In particular, a pyridinethiolate nickel complex prepared from the above-mentioned 3,4-pyridine-dithiol compound is capable of absorbing the near-infrared-rays. Furthermore, since it can achieve hydrogen bonding due to its pyridine skeleton, the pyridinethiolate nickel complex has relatively high solubility in an alcohol solvent and a mixed solvent of alcohol and water and high compatibility with resins, as compared with the conventional near-infrared-rays absorbing materials.

When the pyridinethiolate nickel complex is used as a light stabilizer in an organic-dye-type optical disk, high light stabilizing effect is exhibited, and the bit error ratio, which may be otherwise increased during an extended preservation, can be minimized.

The preparation method of the aforementioned 3,4-pyridine-dithiol compound of formula (I) is regarded as industrially advantageous because the polyhalogenide pyridine compound is easily available as a starting material for producing the pyridinethiolate metal complexes.

Other features of this invention will become apparent in the course of the following description of exemplary embodiments, which are given for illustration of the invention and are not intended to be limiting thereof.

EXAMPLE 1

[Preparation of 3,4-Pyridine-dithiol Compound No. 1]

16 parts by weight of a sodium hydrosulfide with a purity of 70% was placed in a four-necked flask while slowly blowing argon gas through the flask.

70 parts by weight of N,N-dimethylformamide was added to the above sodium hydrosulfide with stirring, thereby preparing a green solution.

After the addition of 3.4 parts by weight of iron powder and 1.6 parts by weight of sulfur to the above-prepared green solution, 20 parts by weight of pentachloropyridine was gradually added to the mixture solution with stirring while water-cooled.

After the addition of the pentachloropyridine to the mixture, it was continuously heated in such a fashion that the temperature of the reaction mixture reached 120° C. in 5 hours. Upon further continued heating, the reaction mixture was refluxed for 15 hours.

After the completion of the reaction, the reaction mixture was cooled to room temperature and 120 parts by weight of water was added thereto with stirring, so that a black product precipitated. This black product was filtered with suction.

The thus obtained black product was placed in a conical flask. To this black product, 150 parts by weight of methanol, and 150 parts by weight of an aqueous solution of 22 parts by weight of zinc oxide and 30 parts by weight of sodium hydroxide were added, and the mixture was refluxed for 1 hour.

After the completion of the refluxing, the mixture was cooled to room temperature and filtered with suction, whereby a deep red filtrate was obtained.

This filtrate was added dropwise to an aqueous solution of concentrated sulfuric acid consisting of 300 parts by weight of water and 150 parts by weight of concentrated sulfuric acid while water-cooled.

Thereafter, orange crystals separated out. These orange crystals were filtered off with suction. By adding a large quantity of chloroform to the crystals, the desired product was extracted. The chloroform was distilled away, so that 12 parts by weight of 2,5,6-trichloro-3,4-pyridine-dithiol was obtained in pale yellow crude crystals in a 60% yield.

The melting point of this crude product was 134.5° to 135.0° C. (gaseous decomposition).

This crude product was recrystallized from chloroform, whereby 3,4-pyridine-dithiol compound No. 1 according to the present invention, which is 2,5,6-trichloro-3,4-pyridine-dithiol, was obtained as light brown columnar crystals.

The melting point of the thus obtained product was 135.5° to 136.5° C. (gaseous decomposition).

The results of the elemental analysis of the 3,4-pyridine-dithiol compound No. 1 according to the present invention were as follows:

|  | % C | % H | % N | % S | % Cl |
|---|---|---|---|---|---|
| Calculated | 24.35 | 0.81 | 5.68 | 26.01 | 43.13 |
| Found | 24.83 | 0.62 | 5.57 | 25.56 | 43.18 |

The calculation was based on the formula for 2,5,6-trichloro-3,4-pyridine-dithiol of $C_5H_2NS_2Cl_3$.

Figure 1:
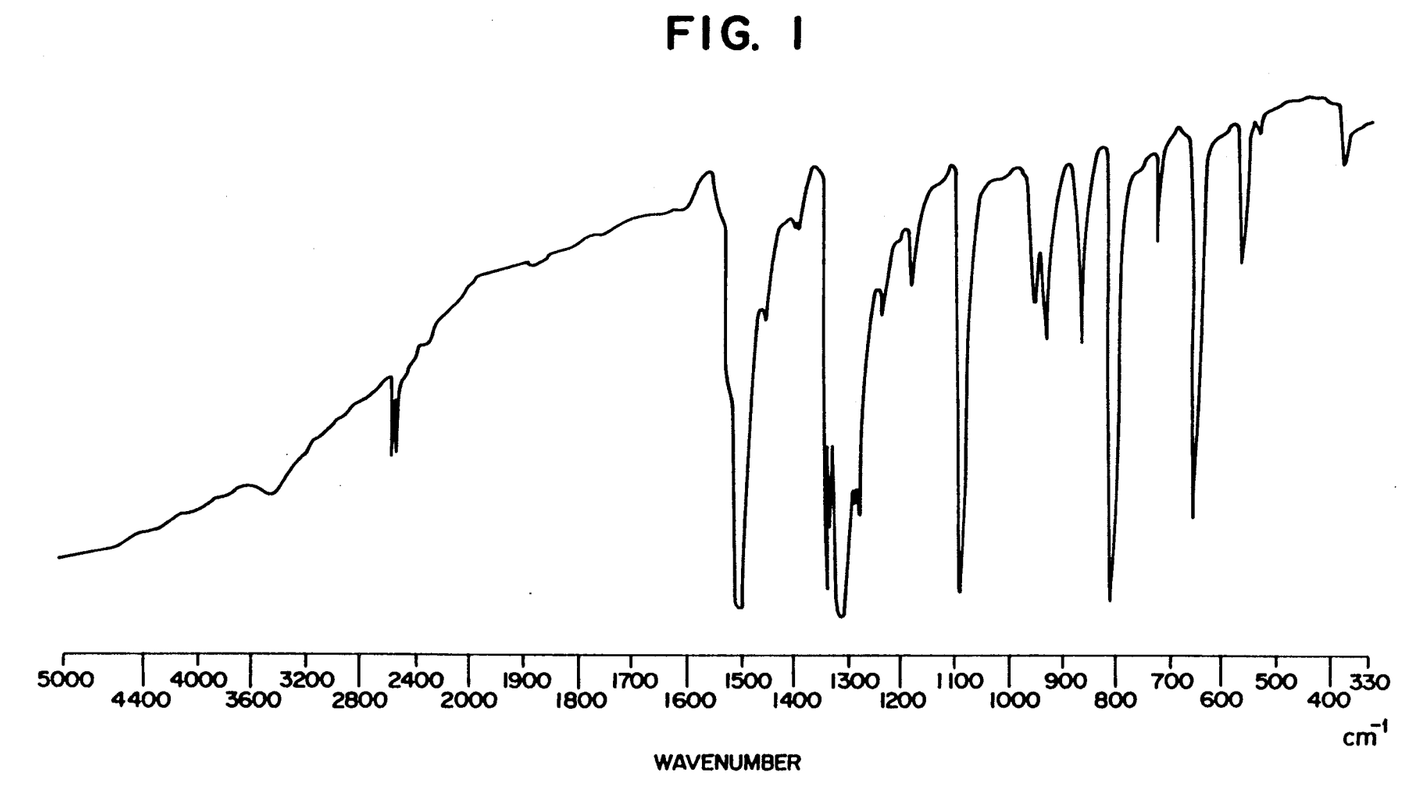
FIGS. 1 and 2 are IR spectra of 3,4-pyridine-dithiol compounds No. 1 and No. 2 according to the present invention, which are obtained in Synthesis Examples 1 and 2, respectively.

FIG. 1 shows an infrared spectrum of the above obtained 2,5,6-trichloro-3,4-pyridine-dithiol, taken by use of a KBr tablet.

Figure 3:
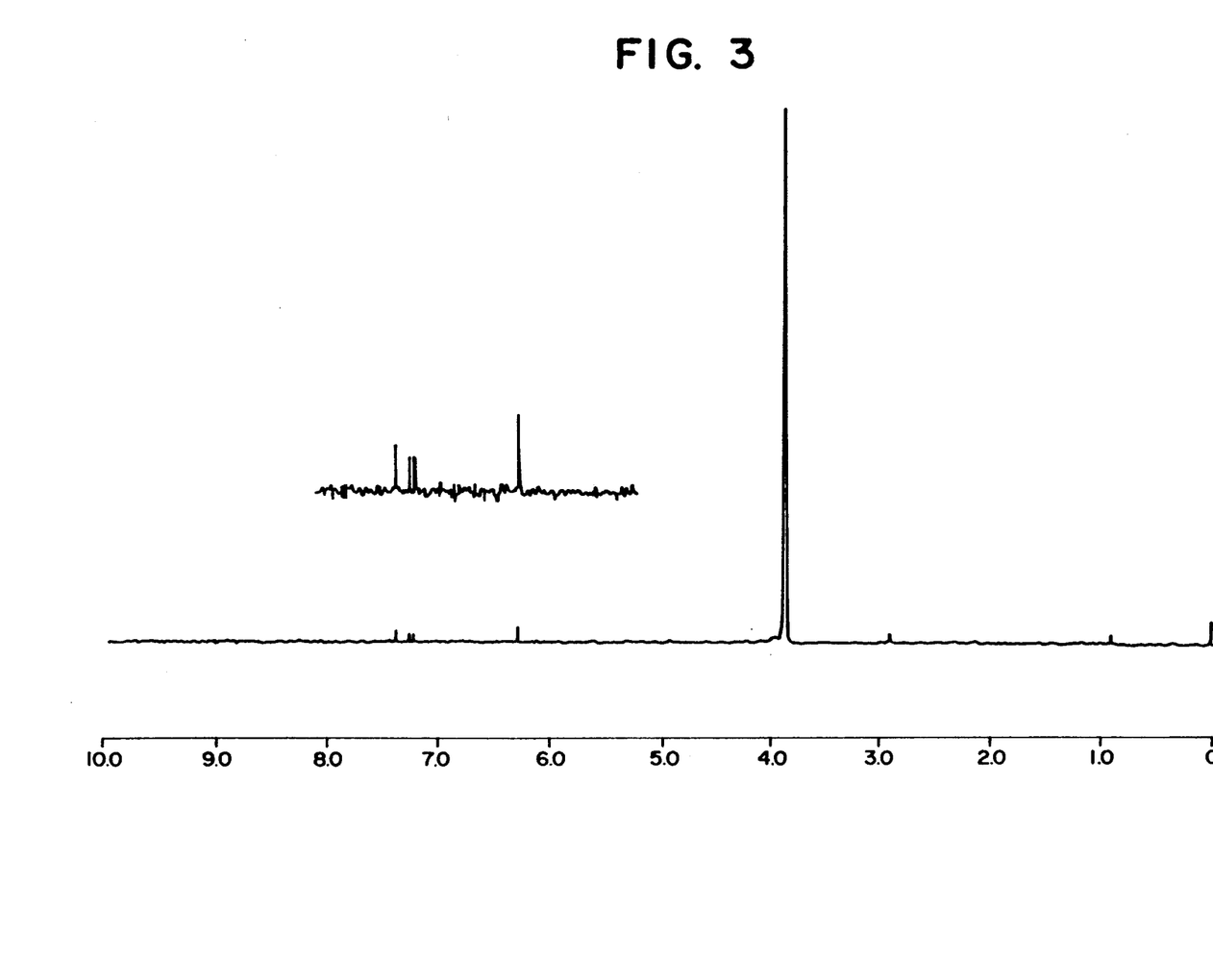
FIG. 3 is $^{13}$C-NMR spectrum of 3,4-pyridine-dithiol compound No. 1 according to the present invention, obtained by using a chloroform solvent.

FIG. 3 shows a $^{13}$C-NMR spectrum of the above 2,5,6-trichloro-3,4-pyridine-dithiol, taken by use of chloroform as a solvent.

Figure 4:
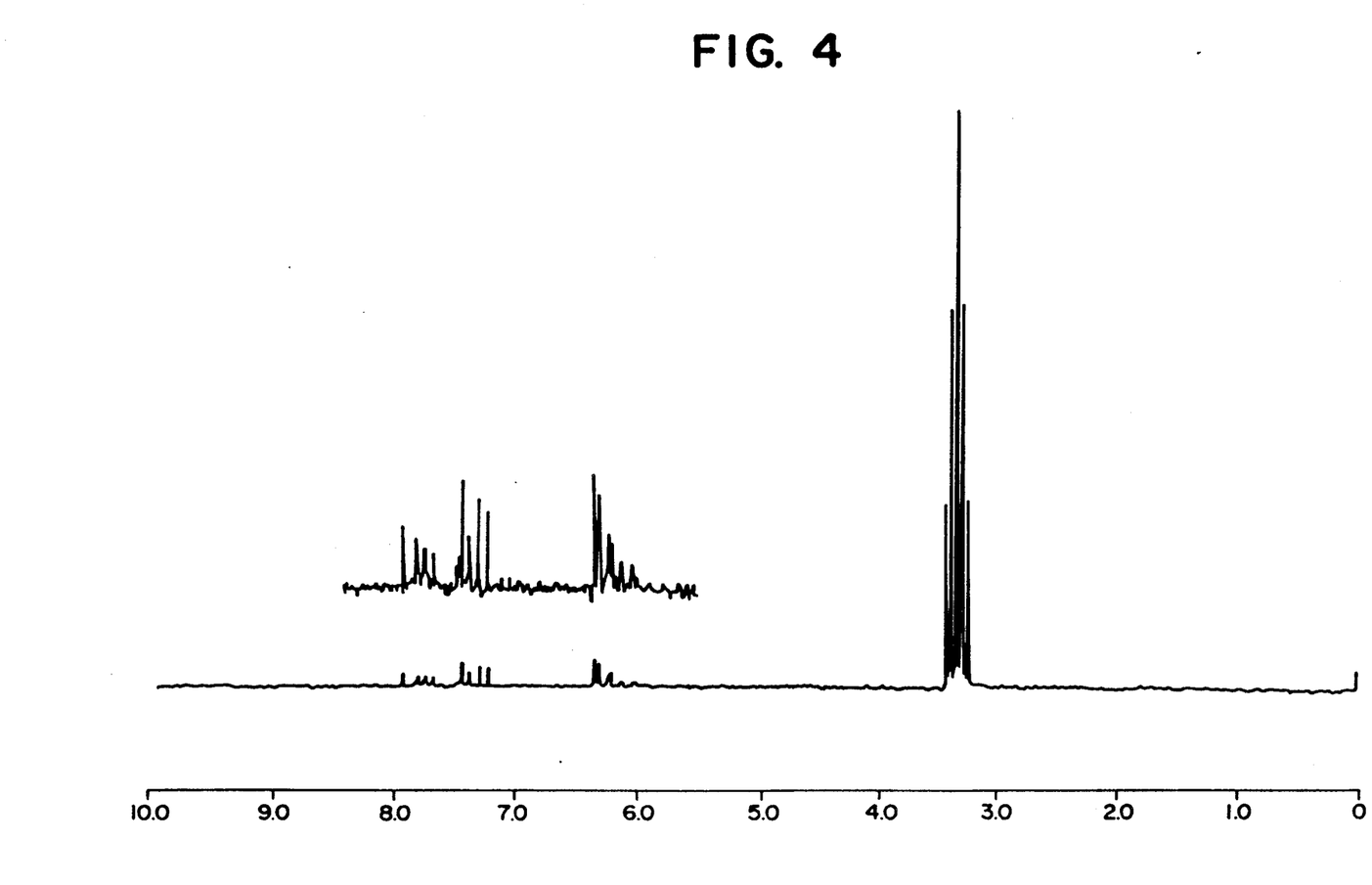
FIG. 4 is $^{13}$C-NMR spectrum of 3,4-pyridine-dithiol compound No. 1 according to the present invention, obtained by using a dioxane solvent.

FIG. 4 shows a $^{13}$C-NMR spectrum of the above 2,5,6-trichloro-3,4-pyridine-dithiol, taken by use of dioxane as a solvent.

Figure 5:
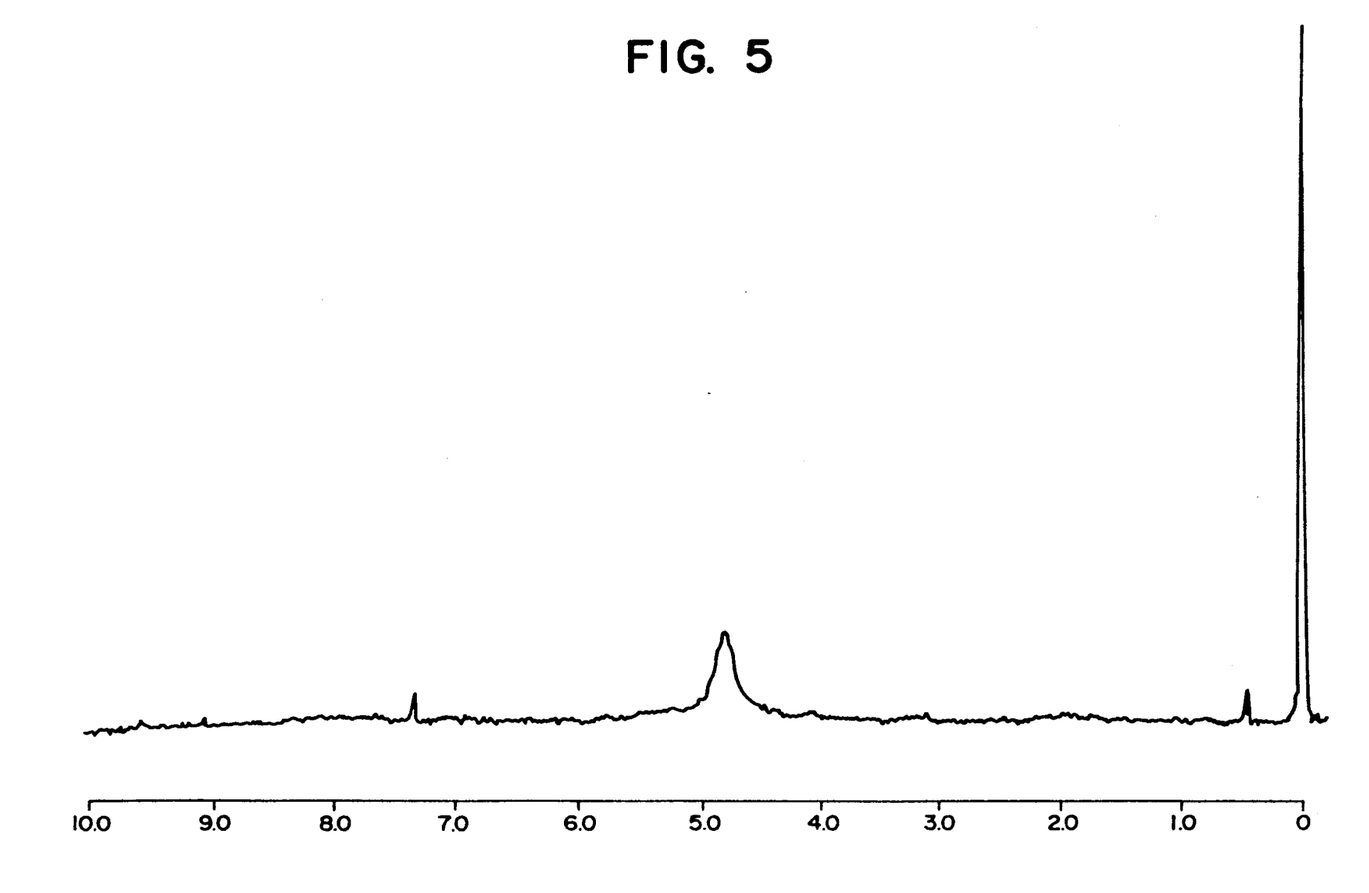
FIG. 5 is $^1$H-NMR spectrum of 3,4-pyridine-dithiol compound No. 1 according to the present invention, obtained by using a chloroform solvent.

FIG. 5 shows a $^1$H-NMR spectrum of the above 2,5,6-trichloro-3,4-pyridine-dithiol, taken by use of chloroform as a solvent.

IR: The absorption peaks were observed at 2550 $cm^{-1}$ and 2590 $cm^{-1}$ characteristic of SH group.

$^{13}$C-NMR: The absorption peaks were observed at 147.97, 145.47, 144.54 and 126.12 ppm in chloroform.

$^{13}$C-NMR: The absorption peaks resulting from the conversion of a moiety of dithiol into a disulfide were observed in dioxane. Among them, five peaks at 148.89, 145.96, 144.62, 127.05 and 126.43 ppm indicated absorption intensity.

$^1$H-NMR: A broad peak was observed at $\delta 4.75$ in chloroform.

EXAMPLE 2

[Preparation of 3,4-pyridine-dithiol Compound No. 2]

The procedure for the preparation of 3,4-pyridine-dithiol compound No. 1 in Example 1 was repeated except that 20 parts by weight of pentachloropyridine employed in Example 1 was replaced by 22.7 parts by weight of 6-trifluoromethyl-2,3,4,5-tetrachloro-pyridine; 3.4 parts by weight of iron powder employed in Example 1 was replaced by 12 parts by weight of $FeCl_2.4H_2O$; and argon gas was replaced by nitrogen gas, whereby 9.2 parts by weight of pyridine-thiol compound No. 2 according to the present invention, which is a mixture of 6-trifluoromethyl-2,5-dichloro-3,4-pyridine-dithiol and 2-trifluoromethyl-5,6-dichloro-3,4-pyridine-dithiol, was obtained as light brown needle-like crystals in a 42% yield.

The melting point of the thus obtained product was 61.5° to 64.0° C.

Figure 2:
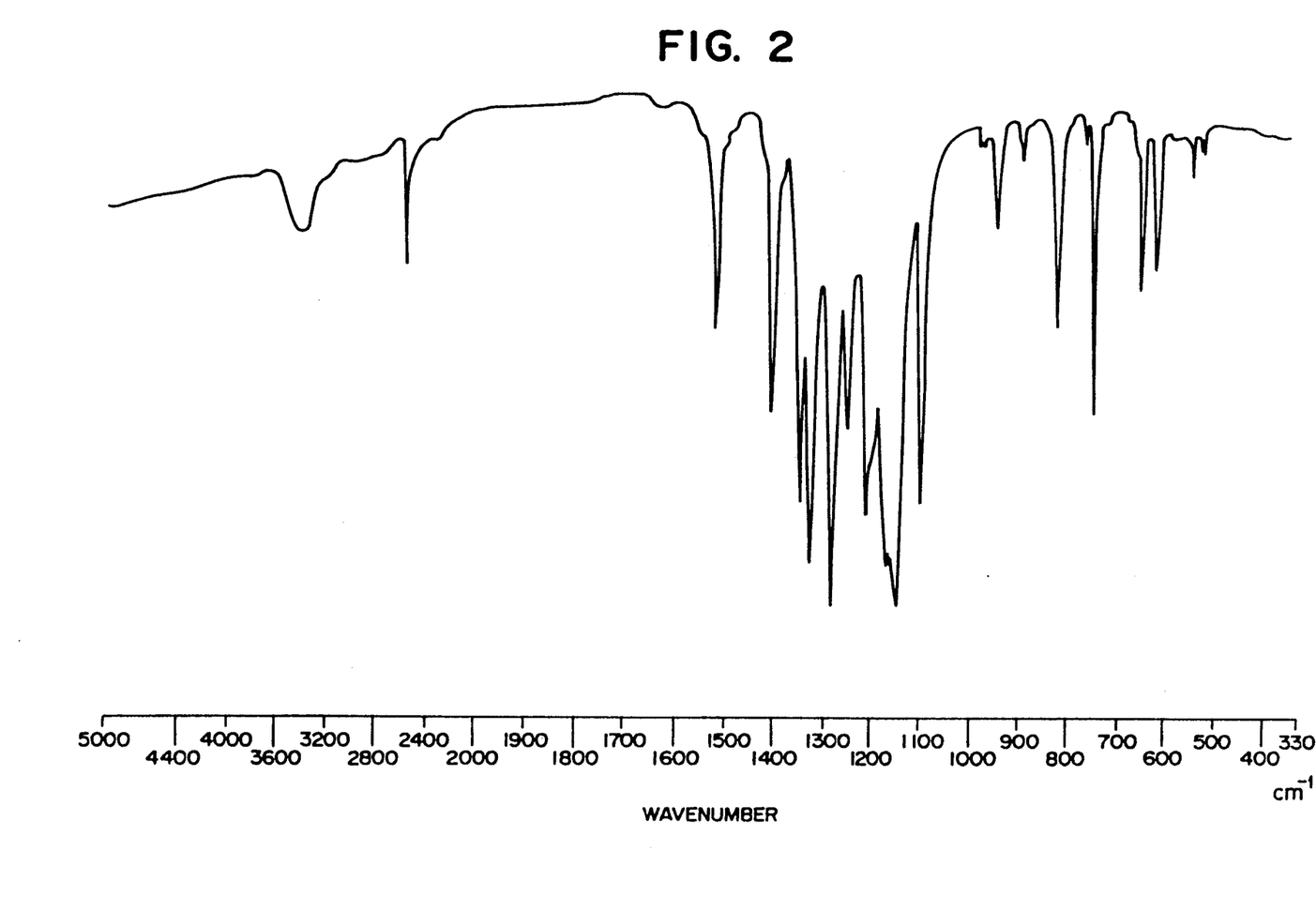

FIG. 2 shows an infrared spectrum of the above obtained 3,4-pyridine-dithiol compound No. 2, taken by use of a KBr tablet, which indicates an absorption at 2590 $cm^{-1}$ and 2600 $cm^{-1}$ characteristic of the SH group in the compound.

COMPARATIVE EXAMPLE 1

The procedure for the preparation of 3,4-pyridine-dithiol compound No. 1 in Example 1 was repeated except that 20 parts by weight of pentachloropyridine employed in Example 1 was replaced by 11.4 parts by weight of 2,3-dichloropyridine, whereby 2.5 parts by weight of comparative compound No. 1 was obtained as a brown-yellow solid. The thus obtained comparative compound No. 1 was scarcely dissolved in chloroform, and proved to be different from the desired 2,3-pyridinethiol.

The melting point of the thus obtained product was 298° C. or more.

The results of the elemental analysis of the comparative compound No. 1 were as follows:

|  | % C | % H | % N |
| --- | --- | --- | --- |
| Calculated | 41.93 | 3.51 | 9.77 |
| Found | 34.20 | 2.18 | 8.00 |

The calculation was based on the formula for 2,3-pyridine-dithiol of $C_5H_5NS_2$.

Figure 6:
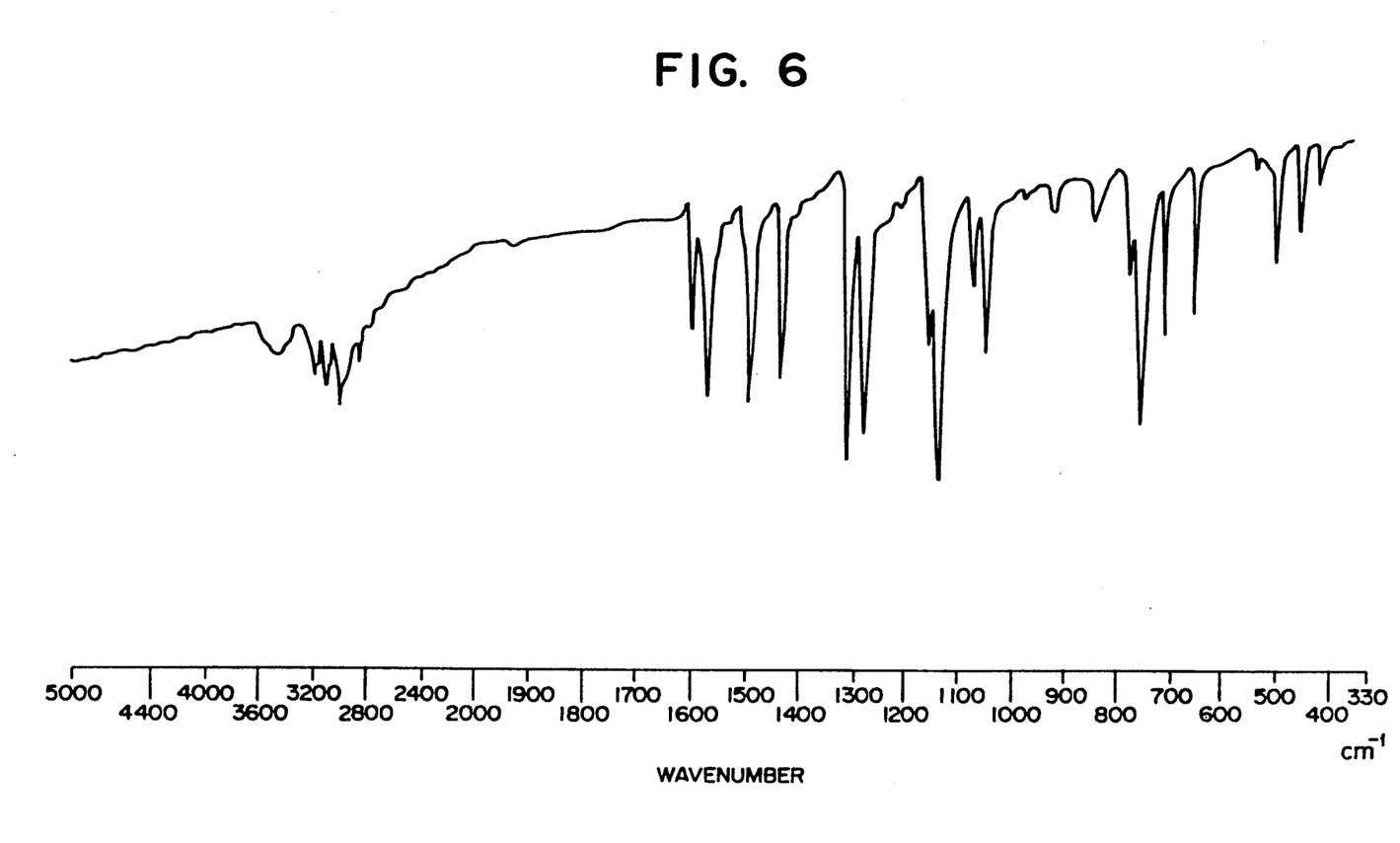
FIGS. 6 and 7 are IR spectra of compounds, which are obtained in Comparative Examples 1 and 2, respectively.

FIG. 6 shows an infrared spectrum of the above obtained comparative compound No. 1, taken by use of a KBr tablet, which does not indicate an absorption characteristic of the SH group.

COMPARATIVE EXAMPLE 2

The procedure for the preparation of the 3,4-pyridine-dithiol compound No. 1 in Example 1 was repeated except that 20 parts by weight of pentachloropyridine employed in Example 1 was replaced by 22.7 parts by weight of 4-trifluoromethyl-2,3,5,6-tetrachloropyridine, whereby 4.8 parts by weight of comparative compound No. 2 was obtained as a brown-red solid.

The melting point of the thus obtained product was 119.0° to 125.0° C.

Figure 7:
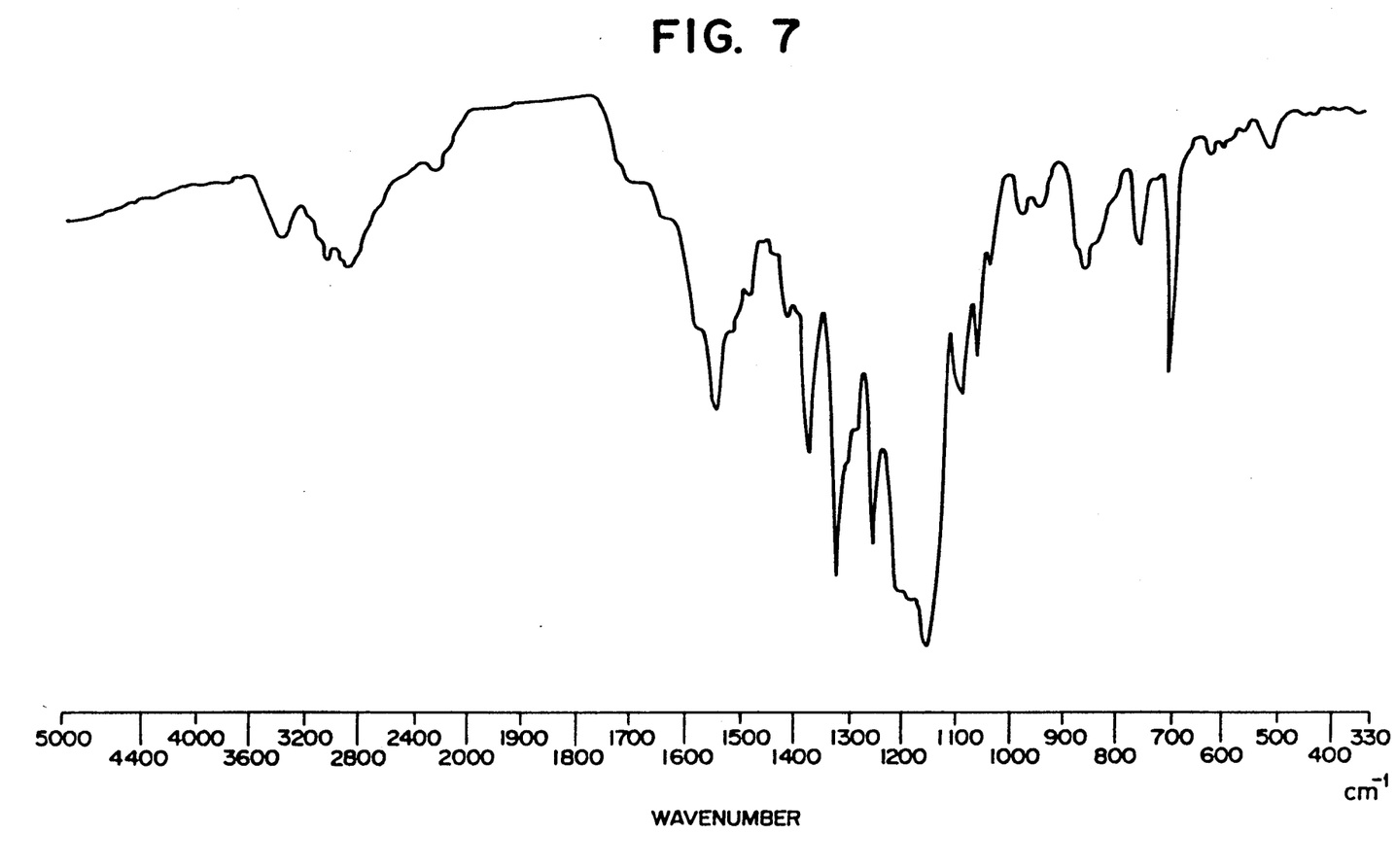

FIG. 7 shows an infrared spectrum of the above obtained comparative compound No. 2, taken by use of a KBr tablet, which does not indicate an absorption characteristic of the SH group. The thus obtained comparative compound No. 2 was proved to be different from the desired 4-trifluoromethyl-5,6-dichloro-2,3-pyridinethiol.

APPLICATION EXAMPLE 1

Preparation of Pyridinethiolate Nickel Complex 10 parts by weight of 2,5,6-trichloro-3,4-pyridinethiol obtained in Example 1 was dissolved in 400 parts by weight of chloroform. To this chloroform solution, an ethanol solution consisting of 4.82 parts by weight of $NiCl_2.6H_2O$ and 67 parts by weight of ethanol was added dropwise with stirring at room temperature. As a result, a red product precipitated.

This red product was separated from the reaction mixture by filtration. The yield was 10 parts by weight.

This product was proved to be a nickel complex with a bivalent negative electric charge or a mixed nickel complex with a bivalent negative charge and a univalent negative electric charge, having no stable counter ion. It is considered that this product is a hydrochloride and/or a hydrate. Hereinafter it is referred to as the hydrochloride for short.

10 parts by weight of the thus obtained hydrochloride was dissolved in a mixed solvent consisting of 140 parts by weight of water and 505 parts by weight of ethanol, and the mixture was stirred at room temperature for 4 hours, with blowing air through the mixture.

After the completion of stirring, 6.1 parts by weight of tetra-n-butylammonium bromide was added to the above mixture solution, thereby precipitating a green product.

This green product was separated from the mixture solution by filtration. The yield was 12.4 parts by weight. This product was purified by column chromatography using 1,2-dichloroethane as a developing solution, whereby tetra-n-butylammoniumbis(2,5,6-trichloro-3,4-pyridinethiolate) nickelate complex with a univalent negative electric charge was obtained.

The thus obtained pyridinethiolate nickel complex showed an absorption at 854 nm in a methanol solvent. The molar absorption coefficient thereof was 8900.

APPLICATION EXAMPLE 2

Preparation of Pyridinethiolate Nickel Complex

One part by weight of the mixture of 6-trifluoromethyl-2,5-dichloro-3,4-pyridinethiol and 2-trifluoromethyl-5,6-dichloro-3,4-pyridinethiol obtained in Example 2 was dissolved in 52 parts by weight of chloroform. To this chloroform solution, an ethanol solution consisting of 0.242 parts by weight of $NiCl_2.6H_2O$ and 10 parts by weight of ethanol was added with stirring at room temperature.

After stirring the reaction mixture for 1.5 hours, 0.575 parts by weight of tetra-n-butylammonium bromide was added to the above mixture solution, with further stirring for 1 hour.

The solvent was distilled away from the reaction mixture, and the residue was purified by column chromatography using 1,2-dichloroethane as a developing solution, whereby two kinds of dark green nickel complexes were obtained.

One had a melting point of 170° to 172° C., and the other had a melting point of 200° to 201.5° C.

Both nickel complexes showed an absorption at 820 nm in a methanol solvent, and the molar absorption coefficient thereof was 10,000.

APPLICATION EXAMPLE 3

Preparation of Optical Recording Medium

Grooves with a half width of 0.3 μm and a depth of 950 Å were formed by injection molding on a disk-shaped substrate made of polycarbonate having a thickness of 1.25 mm and a diameter of 200 mm in the range of 45 to 94 mm away from the center of the substrate, at intervals of a track pitch of 1.6 μm.

A mixture of a dye with the following formula and the nickel complex obtained in Application Example 1 at a mixing ratio by weight of 85 to 15 was dissolved in a mixed solvent consisting of 80 parts by weight of methanol and 20 parts by weight of 1,2-dichloroethane, so that a recording layer coating solution was prepared.

The thus prepared coating solution was coated on the substrate by the spin coating, whereby a recording layer having a thickness of 700 Å was formed on the substrate. Thus, an optical recording medium No. 1 was obtained.

To evaluate the recording characteristics of the above-prepared optical recording medium, information was recorded by applying a semiconductor laser beam having a wavelength of 790 nm to the substrate side of the recording medium, under the conditions of a recording frequency of 0.5 MHz and a line speed of 1.5 m/sec.

Using the same semiconductor laser as in the above, a laser beam was applied to the recording medium to reproduce the recorded information and the light reflected by the recording medium was detected. The detected light was subjected to a spectral analysis, using a scanning filter at a band width of 30 kHz, so that the initial C/N (Carrier/Noise) ratio was obtained.

In addition to the above, the stability of the optical recording medium to the reproduction light was evaluated by conducting a reproduction deterioration acceleration test. In this test, the recording medium was exposed to a tungsten light of 54,000 lux for 20 hours. After the irradiation, the reflectance and the C/N ratio of the recording medium were measured in the same manner as in the above.

Furthermore, to evaluate the preservation stability of the optical recording medium, the recording medium was allowed to stand at 60° C. and 90% RH for 1,000 hours. Then, the reflectance and the C/N ratio of the recording medium were measured in the same manner as in the above.

The results are shown in Table 1.

COMPARATIVE APPLICATION EXAMPLE 1

The procedure for preparing the optical recording medium No. 1 in Application Example 3 was repeated except that the nickel complex obtained in Application Example 1 was replaced by a commercially available nickel complex, "PA1006" (Trademark), made by Mitsui Toatsu Chemicals, Inc., having the following formula, whereby comparative optical recording medium No. 1 was obtained.

The thus obtained comparative optical recording medium No. 1 was subjected to the same tests as in Application Example 3.

The results are shown in Table 1.

TABLE 1

| Recording Medium | Initial Value | | Reproduction-Deterioration Acceleration Test | | Preservation Stability Acceleration Test | |
|---|---|---|---|---|---|---|
| | R % | C/N (dB) | R % | C/N (dB) | R % | C/N (dB) |
| Recording Medium No. 1 | 21 | 56 | 18 | 51 | 17 | 52 |
| Comp. Recording Medium No. 1 | 20 | 47 | 15 | 41 | 12 | 35 |

In the above table, "R" denotes the reflectance.

As can be seen from the results in Table 1, an optical recording medium having high stability to heat and light and improved preservability, which does not substantially deteriorate by the reproduction operation can be obtained by using a metal complex prepared by use of the 3,4-pyridine-dithiol compound according to the present invention.

What is claimed is:

1. A 3,4-pyridine-dithiol compound having formula (I):

wherein X is chlorine or a trifluoromethyl group.

2. The 3,4-pyridine-dithiol compound as claimed in claim 1, wherein said 3,4-pyridine-dithiol compound is selected from the group consisting of 2,5,6-trichloro-3,4-pyridine-dithiol, 6-trifluoromethyl-2,5-dichloro-3,4-pyridine-dithiol and 2-trifluoromethyl-5,6-dichloro-3,4-pyridine-dithiol.

3. The 3,4-pyridine-dithiol compound as claimed in claim 1, wherein said 3,4-pyridine-dithiol compound is 2,5,6-trichloro-3,4-pyridine-dithiol.

4. The 3,4-pyridine-dithiol compound as claimed in claim 1, wherein said 3,4-pyridine-dithiol compound is 6-trifluoromethyl-2,5-dichloro-3,4-pyridine-dithiol.

5. The 3,4-pyridine-dithiol compound as claimed in claim 1, wherein said 3,4-pyridine-dithiol compound is 2-trifluoromethyl-5,6-dichloro-3,4-pyridine-dithiol.

* * * * *